United States Patent [19]

Crossley

[11] 4,327,102
[45] Apr. 27, 1982

[54] CERTAIN 2-(PHENYL SULFINYLMETHYL OR ETHYL) PYRIDINE DERIVATIVES, COMPOSITION CONTAINING SAME AND METHOD OF USING SAME

[75] Inventor: Roger Crossley, Reading, England

[73] Assignee: John Wyeth & Brother Limited, Maidenhead, England

[21] Appl. No.: 232,452

[22] Filed: Feb. 9, 1981

[30] Foreign Application Priority Data

Feb. 20, 1980 [GB] United Kingdom ............... 5668/80
Feb. 20, 1980 [GB] United Kingdom ............... 5669/80

[51] Int. Cl.³ .................... C07D 213/34; A61K 31/44
[52] U.S. Cl. ..................................... 424/263; 546/339
[58] Field of Search ......................... 546/339; 424/263

[56] References Cited

U.S. PATENT DOCUMENTS 2,826,584  3/1958  Cislak ................................. 546/339

OTHER PUBLICATIONS

Plant et al., Chemical Abstracts, vol. 85, No. 15, 108,543y, Oct. 11, 1976.
Bauer et al., Journal of Organic Chemistry, vol. 28, pp. 1323–1328, (1963).

Primary Examiner—Alan L. Rotman
Attorney, Agent, or Firm—George Tarnowski

[57] ABSTRACT

The invention provides a compound of formula I

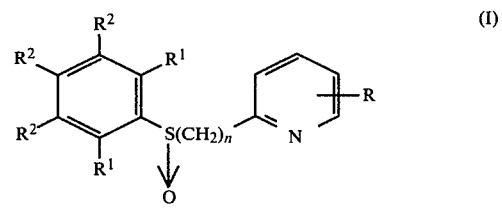

wherein R represents hydrogen, lower alkyl, phenyl, halophenyl, loweralkylphenyl, loweralkoxyphenyl or aralkyl of 7 to 12 carbon atoms, $R^1$ represents hydrogen or fluorine, $R^2$ represents hydrogen, fluorine, chlorine or trifluoromethyl, n is 1 or 2 or pharmaceutically acceptable acid addition salt thereof.

Pharmaceutical compositions containing the compounds are also covered as are methods of treating ulcers or hypersecretion using the compounds. Corresponding thiocompounds, useful as intermediates, are also disclosed.

10 Claims, No Drawings

CERTAIN 2-(PHENYL SULFINYLMETHYL OR ETHYL) PYRIDINE DERIVATIVES, COMPOSITION CONTAINING SAME AND METHOD OF USING SAME

The invention relates to novel sulphur compounds which have activity in tests for anti-ulcer and/or anti-secretory activity.

The invention provides compounds of formula

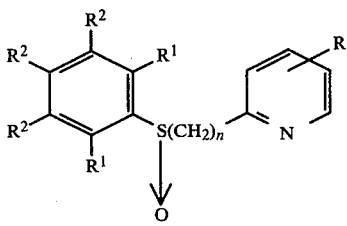

wherein R represents hydrogen, lower alkyl, phenyl, halophenyl, loweralkylphenyl, lower alkoxyphenyl, or aralkyl of 7 to 12 carbon atoms, $R^1$ represents hydrogen or fluorine, $R^2$ represents hydrogen, fluorine, chlorine, or trifluoromethyl, n is 1 or 2, and pharmaceutically acceptable acid addition salts thereof.

Preferably not more than two $R^2$ groups are chlorine or trifluoromethyl.

In this specification a lower alkyl group has from 1 to 6 carbon atoms e.g. methyl, ethyl, n-propyl, isopropyl, n-butyl, s-butyl, t-butyl, n-pentyl and n-hexyl. A loweralkoxy substituent is alkoxy in which the alkyl portion is as defined for a lower alkyl group. Whenever the term lower alkyl is used as part of another radical, e.g. aryl-loweralkyl, the lower alkyl or lower alkoxy portion has 1 to 6 carbon atoms unless otherwise stated.

The acid addition salts of compounds of formula I may be of an organic or inorganic acid, e.g. hydrochloric, hydrobromic, phosphoric, sulphuric, nitric, citric, acetic, formic, fumaric, maleic, tartaric, embonic, methane sulphonic and p-toluene sulphonic acids.

The compounds of formula I and their acid addition salts may be used in pharmaceutical compositions.

For the pharmaceutical compositions any suitable carrier known in the art can be used. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British specification No. 1,284,394.

Anti-ulcer activity was determined by the stress-induced erosion test of Senay & Levine, Proc Soc Exp Biol Med, 124, 1221–3(1967) and anti-secretory activity by the test of H. Shay, D. Sun and H. Gruenstein, Gastroenterology, 1954, 26, 903–13 as exemplified by Beattie et al. J Med Chem 20, 714 (1977). Compounds which possess one or both these activities are considered to be anti-ulcer agents which can be used for the treatment of ulcers or hypersecretion in mammals. The compounds of formula I which we have tested possess one or both of the above activities.

In another aspect the invention provides as an anti-ulcer agent a compound of formula I or an acid addition salt thereof as defined above.

The invention also includes a method for preparing a compound of formula I, or an acid addition salt thereof, which method comprises oxidising a corresponding compound of formula II

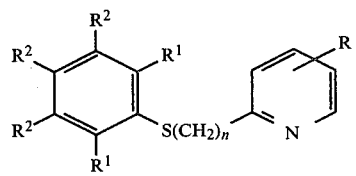

or an acid addition salt thereof wherein R, $R^1$, $R^2$ and n are as defined in connection with formula I, and if desired converting the product to an acid addition salt.

Oxidation may be effected by any suitable means for forming a sulphoxide from a thioether (see Kharasch, Organic Sulphur Compounds, Pergamon Press, New York, 1961, Volume 1, pages 157–159), for example by a per acid or peroxide. Examples of per acids are perbenzoic, m-chloroperbenzoic or peracetic acid. Hydrogen peroxide may also be used. Preferably an acid addition salt of compound II is used in order to prevent or minimise attack of the pyridine nitrogen by the oxidising agent.

The starting materials of formula II are either known compounds or may be prepared by standard methods, e.g. reaction of a thiol compound of formula III, or alkali metal salt thereof

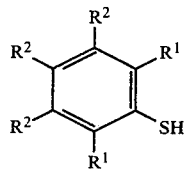

where $R^1$ and $R^2$ are as defined above with a pyridine derivative of formula IV

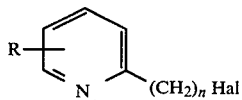

wherein n is 1 or 2 and Hal is a halogen atom, especially chlorine, bromine or iodine and R is as defined above.

The invention includes a method of treating ulcers or hypersecretion in a mammal, which method comprises administering to said mammal an effective amount of a compound of formula I or an acid addition salt thereof. The amount of compound used will depend on the activity of the compound and the needs of the mammal being treated. Doses may range from 1 to 100 mg/kg.

The invention is illustrated by the following Examples:

EXAMPLE 1

2-((Phenylsulphinylmethyl)pyridine)

(A) Thiophenol (21 ml) was added to a solution of sodium (4.6 g) in ethanol (100 ml). To the resulting solution was added 2-picolyl chloride, hydrochloride (15 g) and the mixture was heated at reflux for 2 hours. Precipitated sodium chloride was removed by filtration and the solution was acidified with ethereal HCl. The solvent was removed by evaporation and the residue induced to crystallise by trituration with ether. Recrystallisation from ethanol-ether gave 2-((phenylthio)methylpyridine, hydrochloride (5.0 g) mp 142°–4° C. (Found: C,60.6; H,5.25; N,5.5 $C_{12}H_{11}NS$,HCl requires C,60.6; H,5.1; N,5.9%).

(B) A solution of 2-((phenylthio)methylpyridine, hydrochloride (1 g) in chloroform (10 ml) was cooled to 5° C. and treated with m-chloroperoxybenzoic acid (1 g) and the mixture was stirred for ½ hour. The solution was washed with saturated $Na_2CO_3$ solution dried (MgSO4) and evaporated. The residue was converted into the hydrochloride in ether with ethereal HCl and this use triturated with ether and with acetone to give a solid which was removed by filtration and dried to give the title compound as the hydrochloride (0.8 g) mp 140°–1° C. decomp (Found: C,55.8; H,4.9; N,5.4 $C_{12}H_{11}NOS$, HCl¼H2O requires C,55.65; H,4.7; N,5.5%).

EXAMPLE 2

2-(((4-Chlorophenyl)sulphinyl)methyl)pyridine (A) 4-Chlorobenzenethiol (5 g) in warm ethanol (5 ml) was added to a solution of sodium hydroxide (2.8 g) in ethanol (50 ml). To the solution was added a solution of 2-picolyl chloride, hydrochloride (5.7 g) in ethanol (25 ml) and the mixture was stirred at ambient temperature for 6 hours. The mixture was filtered and evaporated and the residue was converted into the hydrochloride with ethereal HCl solution and this was recrystallised from ethanol-ether to give 2-(((4-chlorophenyl)thio)methyl)pyridine, hydrochloride (8 g) mp 196°–8° C. (Found: C,52.95; H,4.1; N,5.15 $C_{12}H_{10}ClNS$.HCl requires C,53.1; H,4.2; N,4.9%).

(B) A suspension of 2-(((4-chlorophenyl)thio)methyl)pyridine, hydrochloride (2.0 g) in methylene chloride (50 ml) at 0° C. was treated with a solution of m-chloroperoxybenzoic acid (1.7 g) in $CH_2Cl_2$ (25 ml). The mixture was allowed to warm to ambient temperature and was stirred for 5 hours. The solution was washed with saturated sodium carbonate solution and water, then dried (MgSO4). The residue was dissolved in acetone and converted into the hydrochloride with ethereal HCl. N.m.r. showed approximately 20% of starting material remaining so the material was suspended in methylene chloride (50 ml) and treated with further m-chloroperoxybenzoic acid (2×500 g). The solution was washed with saturated sodium carbonate solution and water, dried (MgSO4) evaporated and the residue was dissolved in acetone and the hydrochloride precipitated with ethereal HCl solution. Recrystallisation from acetone-ether gave the title compound as the hydrochloride (0.7 g) mp 170° C. decomp. (Found: C,49.2; H,3.8; N,4.5 $C_{12}H_{10}ClNOS$.HCl.¼H2O requires C,49.2; H,4.0; N,4.8%).

EXAMPLE 3

2-(((3,4-Dichlorophenyl)sulphinyl)methyl)pyridine (A) 3,4-Dichlorobenzenethiol (5 g) was added to a solution of sodium hydroxide (2.25 g) in ethanol (50 ml) and the resulting solution was treated with 2-picolyl chloride, hydrochloride (4.6 g) in ethanol (25 ml). After stirring for 4 hours at ambient temperature the mixture was filtered and the solvent removed by evaporation. The residue was converted into the hydrochloride with ethereal HCl and this was recrystallised from ethanol/ether to give 2-(((3,4-dichlorophenyl)thio)methyl)pyridine, hydrochloride (5.5 g) mp 213°–4° C. (Found: C,46.7; H,3.3; N,4.4 $C_{12}H_9Cl_2NS$.HCl requires C,47.0; H,3.3; N,4.6%).

(B) A suspension of 2-(((3,4-dichlorophenyl)thio)methyl)pyridine, hydrochloride (2.0 g) in methylene chloride (50 ml) at 0° C. was treated with a solution of m-chloroperoxybenzoic acid (1.5 g) in methylene chloride (25 ml). The mixture was allowed to warm to ambient temperature and was stirred for 5 hours. The solution was washed with saturated sodium carbonate solution and water, then dried (MgSO4). The residue was dissolved in acetone and converted into the hydrochloride with ethereal HCl. N.m.r. showed approximately 35% of starting material remaining so the material was suspended in methylene chloride (50 ml) and treated with further m-chloroperoxybenzoic acid (2×500 g). The solution was washed with saturated sodium carbonate solution and water, dried (MgSO₄), evaporated and the residue was dissolved in acetone and the hydrochloride precipitated with ethereal HCl solution. Recrystallisation from propan-2-ol/ether gave the title compound, hydrochloride (0.6 g) mp 178° C. decomp (Found: C44.7; H,3.2; N,4.2. $C_{12}H_9Cl_2NOS.HCl$ requires C,44.7; H,3.1; N,4.3%).

EXAMPLE 4

2-(((4-Fluorophenyl)sulphinyl)methyl)pyridine (A) 4-Fluorobenzenethiol (5 g) was added to a solution of sodium hydroxide (3.14 g) in ethanol (50 ml) and the resulting solution was treated with 2-picolyl chloride, hydrochloride (6.4 g) in ethanol (25 ml) and the mixture was stirred for 6 hours at ambient temperature. The mixture was filtered, the solvent removed by evaporation and the residue was converted into the hydrochloride with ethereal HCl. Recrystallisation from ethanol-ether gave 2-(((4-fluorophenyl)thio)methyl)-pyridine, hydrochloride (7 g) mp 190°–2° C. (Found: C,56.1; H, 4.4; N,5.2 $C_{12}H_{10}FNS.HCl$ requires C,56.4; H,4.3; N,5.4%).

(B) A stirred suspension of 2-(((4-fluorophenyl)thio)-methyl)pyridine, hydrochloride (2 g) in methylene chloride (50 ml) at 0° C. was treated portionwise with m-chloroperoxybenzoic acid (1.8 g) over ½ hour. The mixture was allowed to warm to ambient temperature and the mixture was stirred for a further 4 hours. The solution was washed with saturated Na₂CO₃ solution and water, dried (MgSO₄) and evaporated. The residue was recrystallised from diisopropyl ether to give the title compound (1.0 g) mp 92°–4° C. (Found: C,60.9; H,4.6; N,5.6 $C_{12}H_{10}FNOS$ requires C,61.3; H,4.3; N,5.95%).

EXAMPLE 5

2-(((Pentafluorophenyl)sulphinyl)methyl)pyridine (A) Pentafluorothiophenol (5 g) was added to a solution of sodium hydroxide (2.0 g) in ethanol (50 ml) and the resulting solution was treated with a solution of 2-picolyl chloride, hydrochloride (4.1 g) in ethanol (25 ml). The mixture was stirred at ambient temperature for 4 hours, filtered through Kieselghur and the solvent removed by evaporation. The residue was converted into the hydrochloride with ethereal HCl solution and this was recrystallised from acetone-ether to give 2-(((pentafluorophenyl)thio)methyl)pyridine, hydrochloride (5.0 g) mp 157°–8° C. (Found: C,44.0; H,2.4; N,4.0; $C_{12}H_6F_5NS.HCl$ requires C,44.0; H,2.15; N,4.3%).

(B) A stirred suspension of 2-(((pentafluorophenyl)-thio)methyl)pyridine, hydrochloride (2.0 g) in methylene chloride (50 ml) at 0° C. was treated portionwise with m-chloroperoxybenzoic acid (1.41 g) over ½ hour. The mixture was allowed to warm to ambient temperature, sufficient methylene chloride was added to form a solution, and the mixture was stirred a further ½ hour. The solution was washed with saturated Na₂CO₃ solution and water, dried (MgSO₄) and evaporated. The residue was converted into the hydrochloride in acetone with ethereal HCl solution to give the title compound, hydrochloride (1.3 g) mp 154°–6° C. (Found: C,41.6; H,2.15; N,3.8 $C_{12}H_6F_5NOS.HCl$ requires C41.9; H,2.05; N,4.1%).

EXAMPLE 6

2-(((Trifluoromethylphenyl)sulphinyl)methyl)pyridine (A) m-Trifluoromethylbenzenethiol (5 g) was added to a solution of NaOH (2.25 g) in ethanol (50 ml) and the resulting solution was treated with a solution of 2-picolyl chloride, hydrochloride (4.6 g) in ethanol (25 ml) and the mixture was stirred for 5 hours. The resulting suspension was filtered through kieselghur and the solvent was removed by evaporation. The residue was converted into the hydrochloride in ether with ethereal HCl and recrystallised from acetone-ether to give 2-(((3-trifluoromethylphenyl)thio)methyl)pyridine hydrochloride (4.8 g) mp 145°–6° C. (Found: C,51.1; H,4.0; N,4.7 $C_{13}H_{10}F_3NS.HCl$ requires C,51.0; H,3.6; N,4,6%).

(B) A stirred suspension of 2-(((3-trifluoromethylphenyl)thio)methylpyridine, hydrochloride (2.0 g) in methylene chloride (50 ml) at 0° C. was treated portionwise with m-chloroperoxybenzoic acid (1.5 g) over ½ hour. The mixture was allowed to warm to ambient temperature and the mixture was stirred a further ½ hour. The solution was washed with saturated Na₂CO₃ solution and water, dried (MgSO₄) and evaporated. The residue was converted into the hydrochloride, in acetone with ethereal HCl solution, which was recrystallised from acetone-ether to give the title compound, hydrochloride (1.0 g) mp 135°–6° C. (Found: C,48.3; H,3.7; N,4.0 $C_{13}H_{10}F_3NOS.HCl$ requires C,48.4; H,3.45; N,4.35%).

EXAMPLE 7

2-Methyl-6-((phenylsulphinyl)methyl)pyridine (A) Following the method of Example 1A thiophenol is reacted with 6-methyl-2-picolyl chloride hydrochloride in the presence of sodium ethoxide to give 2-methyl-6-((phenylthio)methyl)pyridine.

(B) A solution of 2-methyl-6-((phenylthio)methyl)-pyridine is reacted with m-chloroperoxybenzoic acid according to the method of Example 1B to give the title compound.

| | Pharmacological Test Results | | | |
|---|---|---|---|---|
| | Stress-induced erosion (Senay & Levine) | | Anti-secretory (Shay et al) | |
| Compound [Product of Example No] | Dose mg/kg | % inhibition | Dose mg/kg | % change in vol |
| 1B | 100 | 60 | 30 | −50 |
| | 30 | NS | | |
| 2B | 100 | NS | 30 | −41 |
| 3B | 100 | 64 | 30 | −40 |
| | 30 | NS | | |
| 4B | 100 | 64 | 30 | −35NS |
| | 30 | NS | | |
| 5B | 100 | 73 | 30 | −53 |
| | 30 | 73 | | |
| 6B | 100 | 64 | 30 | NS |
| | 30 | NS | | |

NS = not significant

PHARMACEUTICAL COMPOSITIONS

The following examples illustrate the preparation of unit dosage form of pharmaceutical compositions according to the invention.

EXAMPLE A

| Antacid Tablet (chewable) | |
|---|---|
| Saccharin | 1.0 mg |
| Hydrated aluminasucrose powder | 750.0 mg |
| 2-((Phenylsulphinylmethyl)pyridine)hydrochloride | 100.0 mg |
| Mannitol BP | 170.0 mg |
| Maize starch BP dried | 30.0 mg |
| Talc purified BP | 28.0 mg |
| Magnesium stearate BP | 20.0 mg |
| Peppermint oil BP | 1.0 mg |
| | 1100.0 mg |

Antacid tablets of the above formulation are prepared by the following procedure. Triturate peppermint oil with talc (screen 40 mesh). Add the triturate, and other ingredients to a blender and mix thoroughly. Slug the powder to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| 2-((Phenylsulphinylmethyl)pyridine | 100.0 mg |
| Celutab | 147.5 mg |
| Mg Stearate | 2.5 mg |
| | 250.0 mg |

The tablets are prepared by the following method. Blend the ingredients in a suitable blender. Compress the blended ingredients on a suitable compression machine to form tablets of the above composition. Celutab is a commercial product comprising 90-2% dextrose, 3-5% maltose, the remainder being higher glucose saccharides. The product is spray crystallised.

EXAMPLE C TO G

Example A is represented but replacing 2-((phenylsulphinylmethyl)pyridine)hydrochloride with 100 mg of the products of Examples 2B, 3B, 4B, 5B, and 6B respectively.

EXAMPLES H TO M

Example B is repeated but replacing 2-((phenylsulphinylmethyl)pyridine)hydrochloride with 100 mg of the products of Examples 2B to 6B respectively.

The invention also concerns novel intermediates of formula II

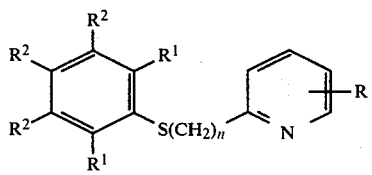

wherein R, $R^1$, $R^2$ and n are as defined in connection with formula I and at least one of R, $R^1$ and $R^2$ is other than hydrogen, and the pharmaceutically acceptable acid addition salts thereof.

I claim:

1. A compound of formula I

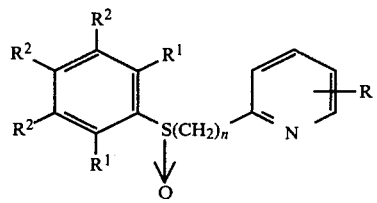

wherein R represents hydrogen or lower alkyl, $R^1$ represents hydrogen or fluorine, $R^2$ represents hydrogen, fluorine, chlorine or trifluoromethyl, n is 1 or 2 or a pharmaceutically acceptable acid addition salt thereof.

2. A compound of formula

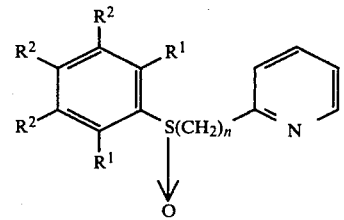

wherein $R^1$ represents hydrogen or fluorine, $R^2$ represents hydrogen, fluorine, chlorine or trifluoromethyl, n is 1 or 2 or a pharmaceutically acceptable acid addition salt thereof.

3. A compound as claimed in claim 1, which is 2(phenylsulphinylmethyl)pyridine or a pharmaceutically acceptable acid addition salt thereof.

4. A compound as claimed in claim 1, which is 2-(((4-chlorophenyl)sulphinyl)methyl)-pyridine or a pharmaceutically acceptable acid addition salt thereof.

5. A compound as claimed in claim 1, which is 2-(((3,4-dichlorophenyl)sulphinyl)methyl)-pyridine or a pharmaceutically acceptable acid addition salt thereof.

6. A compound as claimed in claim 1, which is 2-(((fluorophenyl)sulphinyl)methyl)pyridine or a pharmaceutically acceptable acid addition salt thereof.

7. A compound as claimed in claim 1, which is 2-(((pentafluorophenyl)sulphinyl)methyl)pyridine or a pharmaceutically acceptable acid addition salt thereof.

8. A compound as claimed in claim 1, which is 2-(((3-trifluoromethylphenyl)sulphinyl)methyl)pyridine or a pharmaceutically acceptable acid addition salt thereof.

9. A pharmaceutical composition comprising an anti-ulcer effective amount of a compound as claimed in claim 1 and a pharmaceutically acceptable carrier.

10. A method of treating ulcers or hypersecretion in a mammal, which method comprises orally administering to said mammal in need of such treatment an effective amount of a compound as claimed in claim 1.

* * * * *